(12) United States Patent
Dromms et al.

(10) Patent No.: US 6,422,086 B1
(45) Date of Patent: Jul. 23, 2002

(54) LOW PROFILE PRESSURE MEASURING DEVICE

(75) Inventors: Raymond P. Dromms, Liverpool; Scott W. Osiecki, Skaneateles; Richard L. Vivenzio; Raymond A. Lia, both of Auburn; Scott S. Stearns, Marietta; Dominick A. Danna, Syracuse; James M. Baxter, Jordan, all of NY (US)

(73) Assignee: Welch Allyn, Inc., Skaneateles, NY (US)

( * ) Notice: Subject to any disclaimer, the term of this patent is extended or adjusted under 35 U.S.C. 154(b) by 64 days.

(21) Appl. No.: 09/669,474

(22) Filed: Sep. 25, 2000

(51) Int. Cl.7 .................................................. G01L 7/08
(52) U.S. Cl. ........................................................ 73/715
(58) Field of Search ............................... 73/715, 716, 717, 73/722, 723, 725, 756, 706, 431, 861.18, 861.19; 128/687, 686, 688, 689, 690

(56) References Cited

U.S. PATENT DOCUMENTS

| | | |
|---|---|---|
| 1,106,341 A | 8/1914 | Bristol |
| 1,328,876 A | 1/1920 | Hill |
| 1,377,032 A | 5/1921 | Starling et al. |
| 2,087,494 A | 7/1937 | Annin |
| 2,564,669 A | 8/1951 | Brady |
| 2,636,394 A | 4/1953 | Melchior |
| 3,805,618 A | 4/1974 | Csaposs et al. |
| 3,874,242 A | 4/1975 | Csaposs et al. |
| 4,036,061 A | 7/1977 | Speidel |
| 4,040,298 A | 8/1977 | Lee et al. |
| 4,255,970 A | 3/1981 | VanPottelberg |
| 4,543,824 A | 10/1985 | Marterer |
| 4,653,506 A * | 3/1987 | Romanovskaya ........... 128/677 |
| 4,685,336 A | 8/1987 | Lee |
| 5,181,422 A | 1/1993 | Leonard et al. |
| 5,753,821 A | 5/1998 | Chou |

FOREIGN PATENT DOCUMENTS

| | | |
|---|---|---|
| DE | 0 591 564 A1 | 10/1992 |
| WO | 00/40941 | 7/2000 |

* cited by examiner

Primary Examiner—William Oen
(74) Attorney, Agent, or Firm—Wall Marjama & Bilinski LLP

(57) ABSTRACT

A pressure sensitive device includes a housing having an upper portion and a narrowed lower portion. The housing retains a pressure responsive element having a movable surface which responds to changes in fluid pressure. A movement mechanism interconnects the movable surface of the pressure responsive element with an indicator disposed in an upper portion of the housing wherein at least a portion of the movement mechanism and the pressure responsive element are situated within a narrow lower portion of the housing. The narrow portion includes a ball-shaped end which directly engages a socket of an inflatable sleeve, such as a blood pressure cuff. The interconnection between the ball-shaped end and the socket permits pivotal movement of the housing to facilitate reading of the indicator.

31 Claims, 5 Drawing Sheets

LOW PROFILE PRESSURE MEASURING DEVICE

FIELD OF THE INVENTION

This invention relates to the field of measuring devices, and more specifically to an extremely compact pressure measuring device.

BACKGROUND OF THE INVENTION

Pressure measuring devices, such as sphygmomanometers, typically include a pneumatic bulb which inflates a pressure chamber of an attached sleeve that is fitted over a limb (i.e., an arm or leg) of a patient. A diaphragm or bellows assembly, responsive to changes in fluid pressure of the pneumatic bulb and the sleeve pressure chamber is positioned in a gage housing. A pointer of a dial indicator is interconnected to the bellows assembly by a movement mechanism, whereby inflation of the bellows causes corresponding circumferential movement of the pointer.

Typically, the above referred to movement mechanisms are quite intricate and complex, and are akin in terms of their manufacture and precision to Swiss watches. For example, in one such movement mechanism, a pair of diaphragm springs are attached adjacent opposing ends of a spindle. A bottom end of the spindle is placed in contact with the bellows assembly and a twisted bronze band perpendicularly disposed at the top end of the spindle is connected in parallel by a horizontally disposed bent spring part. As the spindle deflects axially in response to the inflation of the bellows, the bent spring part is also caused to deflect, thereby causing the band to twist. The pointer, attached to the bronze band, therefore is caused to rotate in relation to an adjacent dial face.

Devices, such as the foregoing, include numerous moving and relatively complex components, some or each having multiple bearing surfaces. Therefore, such known devices must be manufactured with relatively strict tolerance margins and their associated costs in terms of both precision and failure rate in order to minimize errors.

In addition, any adjustments required after assembly of the above mechanisms, such as to null the pointer or adjust the sensitivity of the device, require substantial tear-down or at least significant and undesired disassembly.

Furthermore, discrete and separate elements are typically required within the instrument housing for independently supporting the movement mechanism and the bellows assembly, respectively, and for defining an expansion chamber for the bellows assembly therebetween.

A more recent and simplified movement mechanism developed by Applicants and described in U.S. Pat. No. 5,996,829, incorporated by reference in its entirety, includes a vertically disposed axial cartridge having a spirally wrapped ribbon spring with one end mounted to an axially movable elongate shaft and the remaining end to a fixed tubular sleeve. A bottom portion of the shaft is positioned relative to an expandable diaphragm or bellows, wherein subsequent axial translation of the shaft, caused by movements of the diaphragm, elongates the spirally wound ribbon spring and produces repeatable circumferential movement of a pointer supported at the top end of the shaft.

Subsequently, and in order to further reduce the overall size and complexity of the above structure while using the same form of movement mechanism, it has been determined that the diaphragm could be conveniently mounted in sealing relation to the bottom facing side of a single supporting plate. This advance, described in U.S. patent application Ser. No. 09/172,552, also incorporated by reference in its entirety, permits the design of a housing retaining the movement mechanism far more compactly. However, even with this improved design, there is still a continuing general need in the field to further optimize and streamline the housing. There is also a co-existing need in the marketplace to reduce the complexity in the manufacture of pressure measuring devices without compromising their reliability.

Furthermore, numerous pressure measuring devices according to the prior art are typically bulky and relatively heavy. As a result, these devices are easily prone to damage when dropped or otherwise mishandled.

A further problem encountered more specifically with blood pressure measuring devices involves the need for both an inflatable cuff or sleeve and a separate housing which is tethered thereto. Often the instrument housing is difficult to read for the patient who takes their own blood pressure readings or for the doctor or caregiver due to glare against the viewing window of the device or the viewing angle. It is therefore another desired need to be able to more effectively adjust the instrument housing in order to permit easier and more accurate readings.

SUMMARY OF THE INVENTION

It is a primary object of the present invention to provide a pressure measuring device which overcomes the above deficiencies of the prior art.

It is another primary object of the present invention to provide a housing for a pressure measuring device, such as for measuring blood pressure, which is more compact and less expensive to manufacture than previously known devices while being equally reliable.

It is yet another primary object of the present invention to provide a housing for a lightweight, portable pressure sensitive device which can be effectively coupled to an inflatable sleeve, such as a blood pressure cuff.

It is still a further object to provide a pressure measuring device which is lightweight, less resistant to shock or vibration loads, and which is equally reliable in comparison to known devices which are heavier and bulkier.

It is yet another primary object of the present invention to provide a blood pressure measuring device which is easier to use and more convenient than those which are currently available.

Therefore and according to a preferred aspect of the present invention, there is disclosed a shallow profile pressure sensitive device comprising a compact housing having an interior cavity and a sleeve sized to be fitted about the limb of a patient. The sleeve means receives the housing, which includes an indicator disposed an upper housing portion and a narrow lower housing portion sized to be fitted within the receiving means of the sleeve. The lower portion of the housing includes a ball-shaped male engagement member permitting the housing to be pivotally mounted to the sleeve and further permit angled viewing of the indicator. Certain alternatives are easily imagined. For example, the positions of the male and female engagement members could be reversed; that is, a socket could be provided on the instrument housing with the mating end being provided on the sleeve.

Preferably, the housing retains a pressure responsive element disposed within the interior cavity of the housing, the pressure responsive element including a narrowed portion correspondingly fitted within the narrowed portion of the housing. A movement mechanism interconnects a movable surface of the pressure responsive element with the indicator.

According to a preferred version, the movement mechanism includes an axially displaceable shaft member and a ribbon spring member helically wound an axial portion of the shaft member. The ribbon spring includes opposing ends, one of which is attached to a fixed part of the housing and a remaining end which is attached to the shaft member. As the movable surface of the pressure responsive member is caused to move by incoming fluid entering a sealed chamber of the housing from the sleeve, the axially displaceable shaft member is caused to move both axially and circumferentially, producing corresponding indicator movement. In a preferred version, the pressure responsive element is a diaphragm used in connection with a blood pressure cuff.

The sleeve includes a socket sized to receive the ball-shaped engagement end including a port in fluid communication with the sleeve. The housing is, therefore, attached to and capable of both rotational and pivotal movement relative to the sleeve.

According to another preferred version, the housing includes a peripheral bumper guard which protects same from shock or impact loads. Preferably, the guard is attached to the upper housing portion and extends above a viewing window.

According to yet another preferred version, the viewing window further includes an anti-reflective coating to minimize glare.

According to yet another preferred aspect of the present invention, there is disclosed a blood pressure measuring device comprising a housing having an interior cavity, and an inflatable sleeve for wrapping around a patient limb. Disposed within the interior cavity are an indicator mounted within an upper housing portion, a pressure responsive element having at least one movable surface and a movement mechanism interconnecting the at least one moveable surface and the indicator. The housing includes a narrow lower portion including a ball-shaped engagement end for engaging the sleeve such that the housing is pivotally mounted in relation to the sleeve.

In a preferred embodiment, the downwardly extending portion of the housing can be directly coupled to an inflatable blood pressure cuff. This attachment can take place without the need for hoses. Most preferably, the device housing, having a very shallow profile, protrudes slightly from the exterior of the sleeve and is sealed or otherwise attached thereto. Furthermore, in another preferred variation, the housing can be selectively rotated or pivoted with respect to the inflatable sleeve, allowing either the patient or the caregiver to perform and read the measurement.

In another preferred variation, the housing can be used with an RF-welded blood pressure sleeve such that the housing can be attached directly to the inflatable sleeve. A sealed port provided in the sleeve is sized to receive the ball-shaped engagement end of the compact housing.

The proximity of the diaphragm within the housing interior to incoming fluid and the positioning of the movement mechanism within the attachment cavity of the housing affords significant overall savings in the overall profile of the device and therefore allows the above attachment to be extremely efficient.

Preferably, the viewing window of the device housing includes an anti-reflective coating to minimize glare.

An advantage provided by the present device is that the gauge housing can be coupled directly to a blood pressure sleeve or cuff without any interconnecting hoses, providing a highly compact and efficient design with fewer parts.

Furthermore, the overall compactness of the lightweight housing design permits use in literally any form of measuring device, medical or industrial, having a pressure sensitive element including, but not limited to, valves, gauges, switches, and leak detectors.

Yet another advantage of the present invention is a lightweight pressure sensitive housing as described herein allows improved and simplified manufacturability and versatility, but without compromising reliability.

These and other objects, features, and advantages will become apparent from the following Detailed Description which should be read in conjunction with the accompanying drawings.

DETAILED DESCRIPTION

The present invention is herein described with reference to several preferred embodiments, each of which relates specifically to blood pressure measuring apparatus. However, it should be evident to one of sufficient skill in the field that other variations and modifications can be made utilizing the inventive concepts described herein, as well as alternate applications other than blood pressure measurement, including use in barometers, pressure vessel indicators, pressure sensitive switches, valves, and literally any industrial or medical device requiring a pressure responsive element. Furthermore and throughout the course of the following discussion, terms such as "upwardly", "downwardly", "upper", "lower", "top", "bottom", horizontally", "vertically", and the like are used to provide a frame of reference with regard to the accompanying figures. These terms, however, should not be treated as limiting with regard to the invention as herein described.

Figure 1:
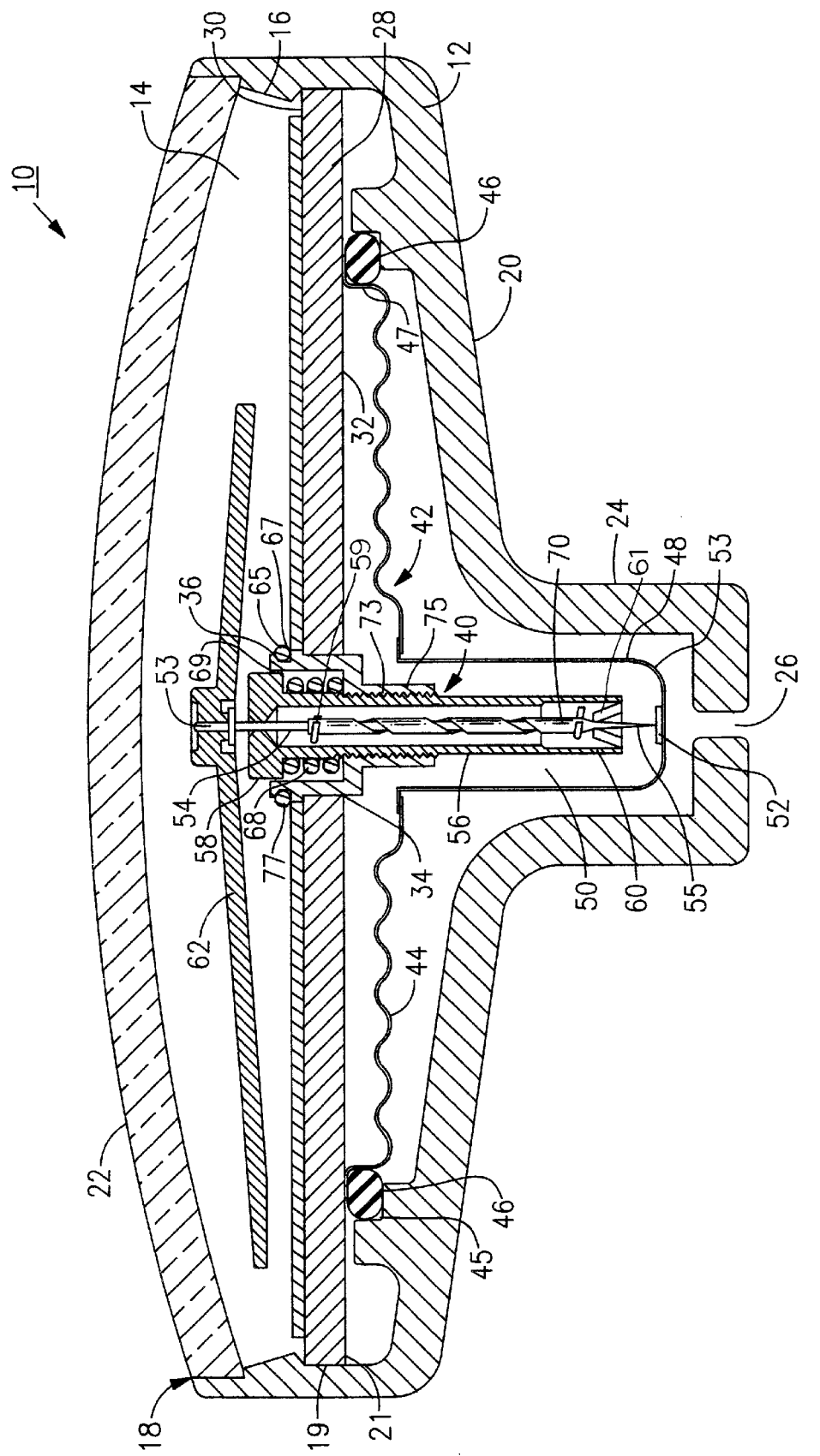
FIG. 1 is a sectional view of a pressure measuring device having a housing made in accordance with a first embodiment of the present invention.

Referring to FIG. 1, there is shown a pressure measuring device 10 made in accordance with a first embodiment of the invention. The device 10 includes a substantially cylindrical housing 12 having an interior cavity 14 defined by a circumferential inner wall 16, an open top end 18, and a bottom end 20. A viewing window or bubble 22, made from glass, plastic, or any suitable transparent material, is attached in a known manner to the open top end 18 of the housing 12. The bottom end 20 of the housing 12 has a diameter which inwardly tapers down to a narrow downwardly extending portion 24 having a bottom opening 26 serving as a port for admitting a fluid. Preferably, the diameter of the narrow extending portion 24 is about one third that of the major portion of the housing 12, though it will be apparent from the following discussion that this parameter can be suitably varied depending upon the application.

The interior cavity 14 of the housing 12 is sized for retaining a number of component parts, including a horizontally disposed support plate 28. The support plate 28 is a generally planar member having opposing top and bottom facing sides 30, 32, and a central through opening 34. A press-fitted sleeve 36 attached to the top facing side 30 of the support plate 28 extends into the central through opening 34 of the support plate 28 and is used for retaining a movement mechanism 40, described in greater detail below. The circumferential inner wall 16 of the housing 12 further includes a reflexed portion 19 which is sized for supporting an outer edge 21 of the horizontal support plate 28 immediately therebeneath and at a predetermined height within the housing 12. The central through opening 34 is shown as being substantially aligned with the bottom opening 26 of the housing 12 according to this embodiment, but this alignment is not essential to the workings of the invention.

A diaphragm subassembly 42 includes a flexible diaphragm 44 which is non-fixedly attached to the bottom facing side 32 of the horizontal support plate 28. The diaphragm 44 is substantially and horizontally planar and includes a plurality of wave-like surfaces 49. An outer edge 47 of the diaphragm 44 is clamped by an O-ring 46 disposed on a circumferential ledge 45 extending upwardly from the bottom end 20 of the housing 12. The O-ring 46 not only supports the diaphragm 44 in place, but also provides a seal, the function of which is described in greater detail below.

According to the invention, the centermost portion of the horizontally planar diaphragm 44 includes a downwardly extending section, hereinafter referred to as the pan 48, which is soldered or otherwise fixed to or integral with the remainder of the diaphragm. The pan 48 is a hollow cylindrical section which extends into the downwardly extending portion 24 of the housing 12 when assembled and includes a cavity 50 having a width dimension that is substantially equal to that of the press-fitted sleeve 36. A lower end 53 of the pan 48 includes a hardened contact surface 52 on the interior thereof.

Still referring to FIG. 1, the movement mechanism 40 according to the present embodiment includes an axially displaceable shaft member 54 which is wholly enclosed within a tubular member 56 with the exception of protruding top and bottom ends 53, 55, respectively. A thin flexible ribbon-like spring section 70 is fixedly attached at one end 61 adjacent the bottom end 55 of the tubular member 56 and at an opposite remaining end 59 to the axially displaceable shaft member 54 around which the ribbon spring 70 is helically or spirally wound. The outer tubular member 56 includes a set of external threads 73 extending over an upper portion of the length thereof which engage corresponding internal threads 75 provided in the press-fitted sleeve 36. The ribbon-like section 70 is manufactured from beryllium copper, spring steel, or other similar material.

The hollow tubular member 56 includes an integral top cap portion 58 having a diameter which is larger than the remainder of the member, the cap portion having a shoulder 57 which bears against a biasing spring 68 disposed within an annular recess 68 of the press-fitted sleeve 36. As described in greater detail below, the top cap portion 58 and the biasing spring 68 are used to adjust the overall sensitivity of the movement mechanism 40.

When correctly positioned, the majority of the movement mechanism 40 extends beneath the horizontal support plate 28 and into the cavity 50 defined in the pan 48 which is already positioned in the downwardly extending portion 24 of the housing 12. In this position, the bottom end 55 of the shaft member 54 is proximate the hardened contact surface 52.

A dial face 63 having measuring indicia (not shown) is attached to the top facing side 30 of the horizontal support plate 28 through a center opening which is sized to fit over the press fitted sleeve 36. An O-ring 65 disposed in a slot 67 of the tubular sleeve 36 engages an inner edge of the dial face 63 with an indicating member 62 being mounted to the protruding top end of the shaft member 54. A preferred lightweight indicating member design useful in this design is described in U.S. Ser. No. 09/471,847, the entire contents of which are herein incorporated by reference.

In operation, changes in the pressure of incoming fluid (in this example, air) entering the bottom opening 26 of the housing 12, and more particularly entering the interior cavity 14 of the housing 12, cause corresponding movements of the diaphragm 44. That is, the seal provided onto the outer edge 47 of the diaphragm 44 by the O-ring 46 clamping against the bottom facing side 32 of the horizontal support plate 28 prevents air from further penetrating the interior cavity 14. Therefore, the increase in pressure causes axial movement of the diaphragm pan 48 with the interior contact surface 52 being caused to push upwardly against the bottom end 55 of the axially displaceable shaft member 54. As a result of the upward movement of the diaphragm 44, the ribbon spring 70 is caused to extend against the fixed end 60 of the tubular member 56, causing the shaft member 54 to rotate about its linear axis. The rotation of the axially displacement shaft member 54 therefore causes a corresponding circumferential movement of the indicating member 62 attached to the top end 53 of the shaft member 34 relative to the measuring indicia (not shown) provided on the dial face 63.

Zero adjustment of the above device 10 is a relatively simple procedure, as compared with previously known devices. First, the bubble or viewing window 22 is removed from the open top end 17 of the housing 64. The engagement of the O-ring 65 against the inner edge of the dial face 63 allows the dial face to be freely rotated in relation to the position of the indicating member 62. Sensitivity adjustments can also be made at the top of the device 10 by rotating the top cap portion 58 against the biasing spring 58 within the recess 69 of the press-fitted sleeve 36, so as to adjust the sensitivity of the ribbon spring 70 for a given rotation. A similar mechanism is described in U.S. Ser. No. 09/172,552, the entire contents of which have previously been incorporated by reference.

Figure 2:
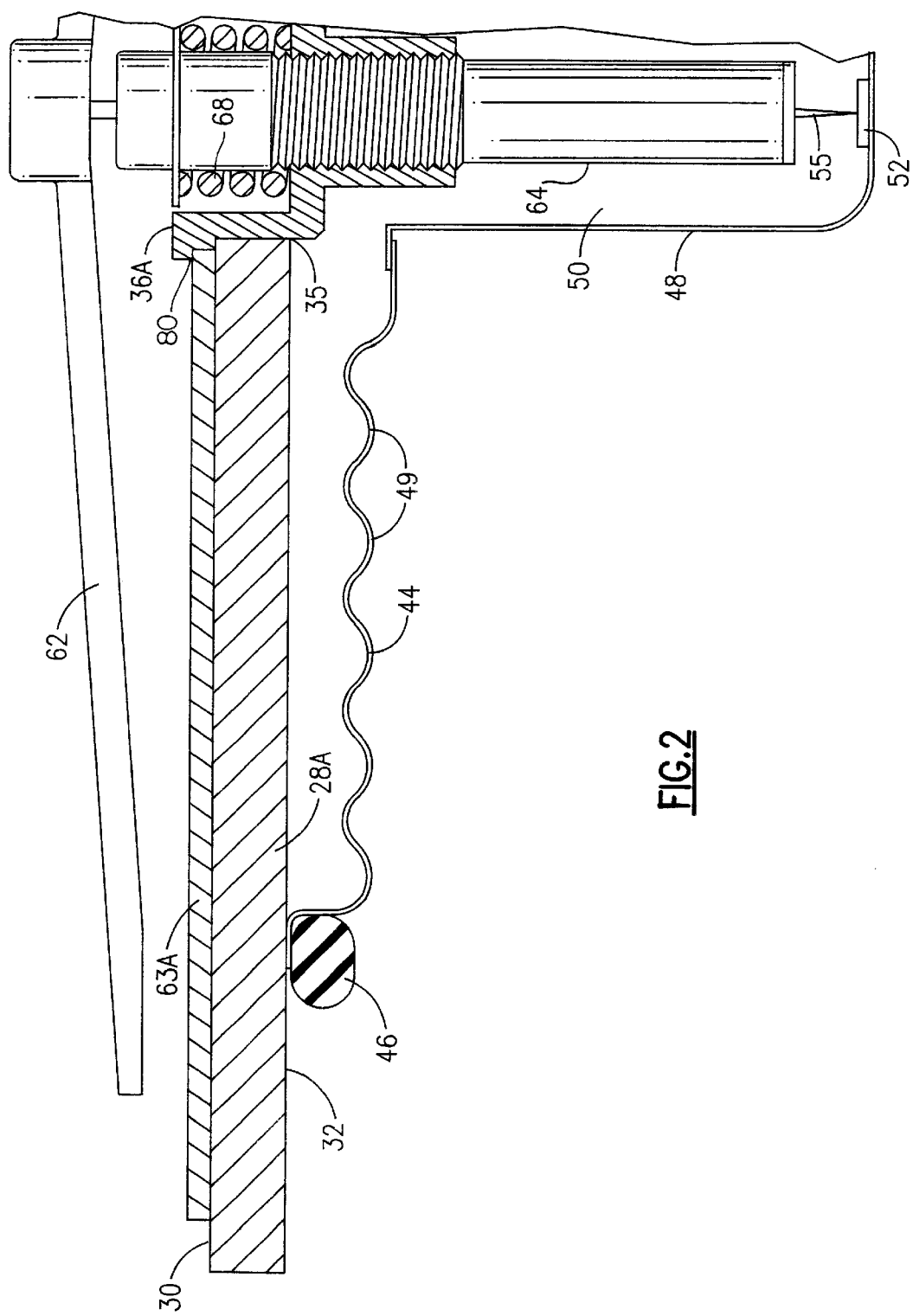
FIG. 2 is an enlarged sectional view of the pressure measuring device of FIG. 1, depicting alternate means for attaching a rotatable dial face in relation to the device.

Variations of the above device are possible. For example and referring to FIG. 2, and in lieu of the O-ring 65 of FIG. 1, either the dial face 63A and/or the horizontal support plate 28A can be suitably tapered adjacent their center openings relative to a slot 80 provided in the sleeve 36A in order to allow the dial face to be rotated without requiring removal. Alternately, the movement mechanism 40 can include a zero adjustment feature as described in the previously incorporated U.S. Ser. Nos. 08/972,583 and 09/172,552. In passing, it should be noted that FIG. 2 only illustrates a portion of the overall assembly in order to distinctly facilitate the above discussion.

Figure 3:
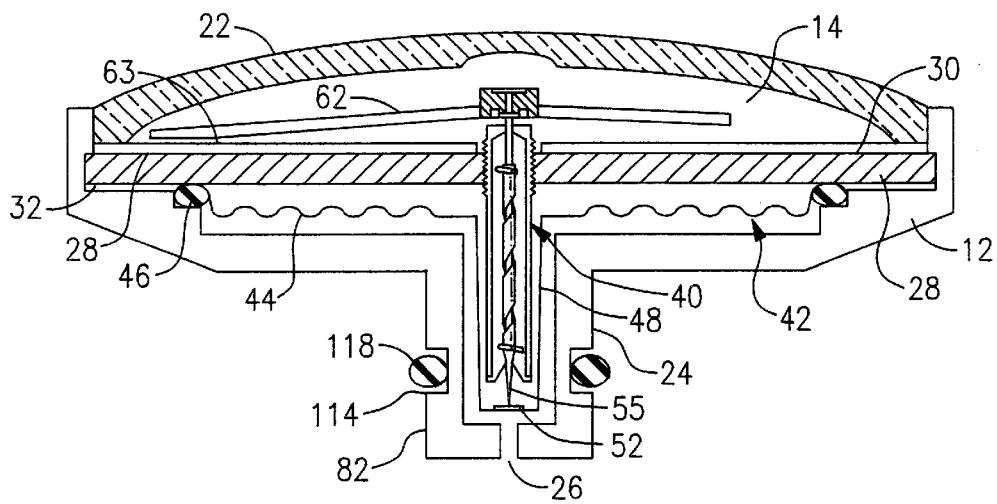
FIG. 3 is a sectional view of a pressure measuring device having a housing made in accordance with a second embodiment of the invention.
Figure 5:
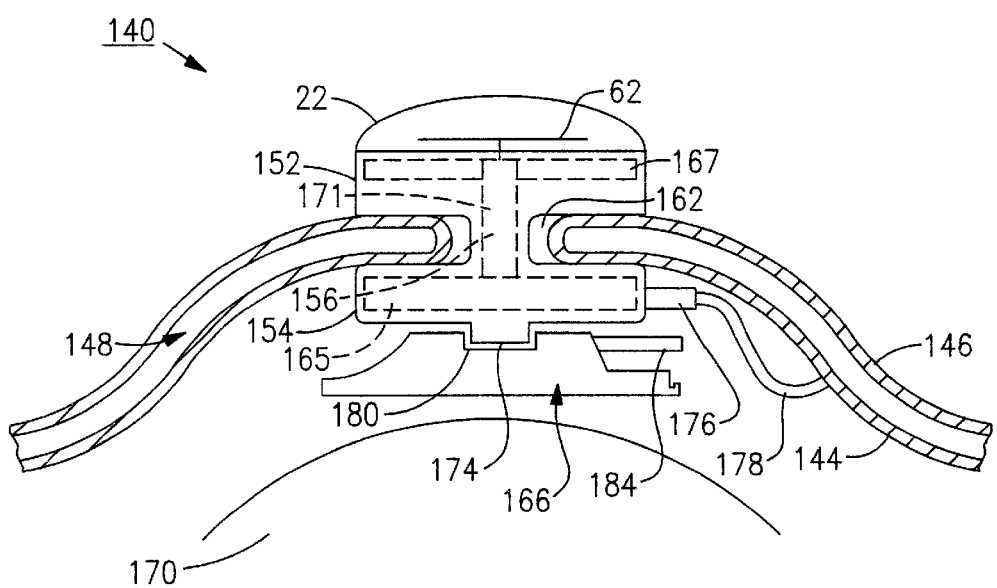
FIG. 5 is a partial sectional view of an pressure measuring device made in accordance with a fourth preferred embodiment of the present invention as used with an inflatable blood pressure sleeve.

A housing design in accordance with a second embodiment is illustrated in FIG. 3. Similar parts are herein labeled with the same reference numerals for the sake of clarity. As in the preceding, the device includes a housing 12 having an interior cavity 14 sized for retaining a diaphragm 42 and a substantially horizontally disposed support plate 28, the housing further having a downwardly extending narrowed portion 24. A movement mechanism 40 is disposed through a central opening 34 defined in the support plate 28 such that the bottom end 55 of an axially displaceable shaft 54 of the mechanism is disposed in proximity to a hardened contact surface 52 of a downwardly extending portion or pan 48 of the diaphragm 44. The diaphragm 44, in the meantime, is attached, but sealed to the bottom facing side 32 of the horizontal support plate 28.

Fluid, such as air, entering an interior cavity 14 of the housing 12 through a bottom opening 26 causes deflection of the pan 48 of the diaphragm 44 against the axially displaceable shaft 54, thereby causing rotation of the shaft by means of an attached ribbon spring 70, according to the manner previously described. Rotation of the shaft 54 produces subsequent circumferential movement of an indicating member 62 in relation to a dial face 63 placed on the top facing side 30 of the support plate 28 which can be seen through a transparent bubble or viewing window 22 of the housing 12.

According to this particular embodiment, the device includes a docking hub 82 provided on the exterior of the narrow downwardly extending portion 24 of the housing 12, the hub including a circumferential slot 114 which is sized for retaining an O-ring 118 or other similar sealing element. For example, the docking hub 82 can utilize pipe threads (not shown). The docking hub 82 provides adequate modification to allow the device to be attached to other existing pressure device housings, having pressure sources for example, those manufactured by Welch Allyn, Inc., or others. In passing, it should be noted that the position of the bottom opening 26 of the housing 12 is not essential; that is, incoming fluid can enter the interior cavity 14 from a horizontally or otherwise disposed port, so long as the opening is beneath the seal provided by the O-ring 118.

To further illustrate variations, a third embodiment of a housing 81, made in accordance with the present invention, includes a diaphragm 84, which unlike the preceding embodiment, is a substantially vertical member having an overall width dimension that is considerably narrower than those previously described. As a result, a horizontal support plate 86 does not require fitting to the circumferential inner wall 16 of the housing 81, the plate being positioned suitably by known means within a cavity 51 provided in the bottom end 88 of the housing 81.

Like the preceding embodiments, an outer edge 90 of the diaphragm 84 is sealed using an O-ring 92 which effectively clamps the outer edge to a bottom facing side of the support plate 86. A movement mechanism 40 is disposed essentially beneath the support plate 86 through a center opening in a press fitted sleeve 96 and threaded into engagement therewith. The majority of the movement mechanism 40 is disposed within the cavity defined by the essentially vertical diaphragm 84, the particular diaphragm of this embodiment having vertically disposed wave-like surfaces 100. Adjustments to control the sensitivity of the movement mechanism 40 using biasing spring 104 are performed in the manner previously described.

Overall, the housing of the instant embodiment defines a very shallow profile in the upper portion of the housing 81. Though not shown, the bottom end of the housing 81 can be used as a docking hub to secure the housing into other gauge housings (not shown) either as a retrofitted or new assembly as previously described above.

Figure 4:
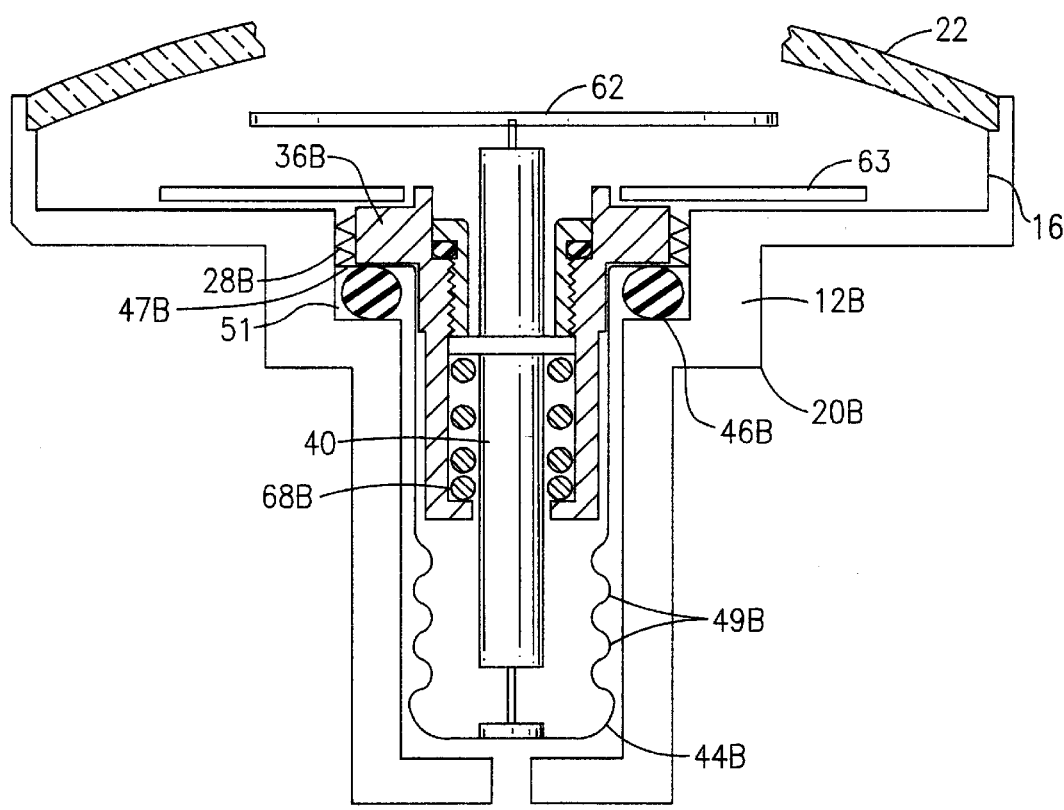
FIG. 4 is a sectional view of a pressure measuring device having a housing made in accordance with a third embodiment of the invention.

Referring to FIG. 4, a housing 140 formed in accordance with a fourth embodiment of the present invention is herein described in combination with a blood pressure sleeve or cuff 142. For purposes of the present embodiment, the instrument housing 140 is used with a specific inflatable blood pressure cuff or sleeve which is described in greater detail in U.S. Pat. No. 6,036,718, the contents of which are hereby incorporated in their entirety. In brief, the inflatable cuff 142 is manufactured using a pair of sleeve portions 144, 146 which are sealed together using continuous RF (Radio Frequency) welds to form an integral structure and define an inflatable inner volume 148. The cuff 142 is then wrapped around the arm 170 or other limb of a patient (not shown) in a manner commonly known.

The housing 140 described according to the present embodiment includes an upper portion 152, a lower portion 154 and a connecting intermediate portion 156. The upper and lower portions 152, 154 are substantially cylindrical and have approximately the same dimensions while the intermediate portion 156 has a substantially smaller diameter that is considerably narrower than either adjoining section, thereby defining a configuration shaped somewhat like a yo-yo. According to the present embodiment, the intermediate portion 156 has a diameter which is approximately one third the diameter of the remaining sections 152,154, but it will be readily apparent that this parameter can be varied depending on the relative size of the movement mechanism used therein. Each of the above sections 152, 154, 156 are hollow and combine to form an interior cavity 158.

According to this embodiment, a horizontal support plate 165 (shown in phantom) is positioned within the lower section 154 of the housing 140 while a dial face 167 (also shown in phantom) is disposed in the upper section 152. A movement mechanism 171 (also shown in phantom), which is similar structurally to those previously described, interconnects the dial face 167 and the support plate 165 and is located primarily in the intermediate portion 156.

According to this embodiment, a slot 162 is cut into the sleeve portions 144,146. The slot 162 provides a button-like retainment for the lower portion 154 and the narrow intermediate portion 156, with the upper portion 152 protruding from the exterior of the cuff 142. A port 176 is connected via a hose 178 to the inflatable inner volume of the cuff 142 which is inflated by a pneumatic bulb (not shown) in a well known manner.

In operation, the device operates similarly to that previously described except that a detachable stethoscope adapter 166 can also be releasably attached to the bottom of the housing 150, therein forming an integral unit. The bottom of the housing 150, according to this embodiment, includes an extending attachment portion 174 sized to engage a female connector 180 or other suitable means provided on the adaptor. All preceding known cuffs require separation between the cuff and the stethoscope. With the overall shallow profile of the above housing 150, use of an adaptor 166 is made worthwhile.

The stethoscope adapter 166 is a conical member which forms the bell of the stethoscope having connecting ear pieces (not shown) attached to a port 184. In use, the adapter 166 is freely rotatable relative to the housing 140, allowing examination by a patient or a care giver to be performed equally well.

Figure 6:
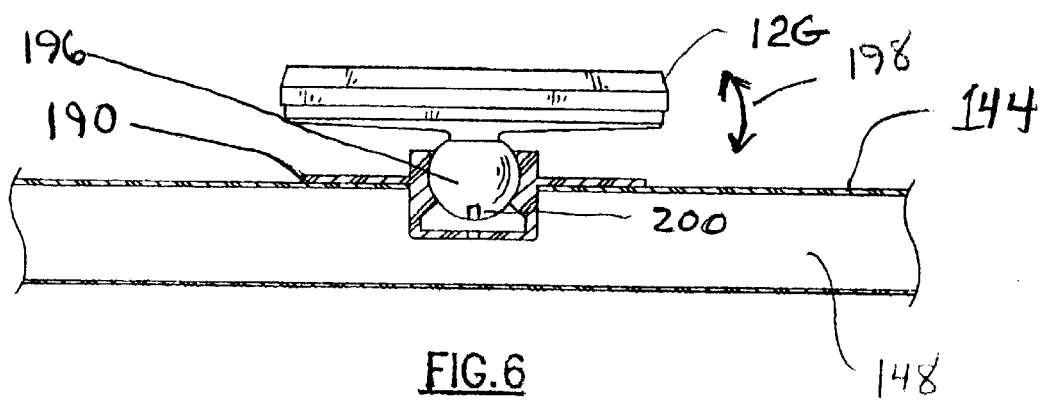
FIG. 6 is a partial perspective view of a pressure measuring device made in accordance with a fifth preferred embodiment of the present invention.
Figure 7:
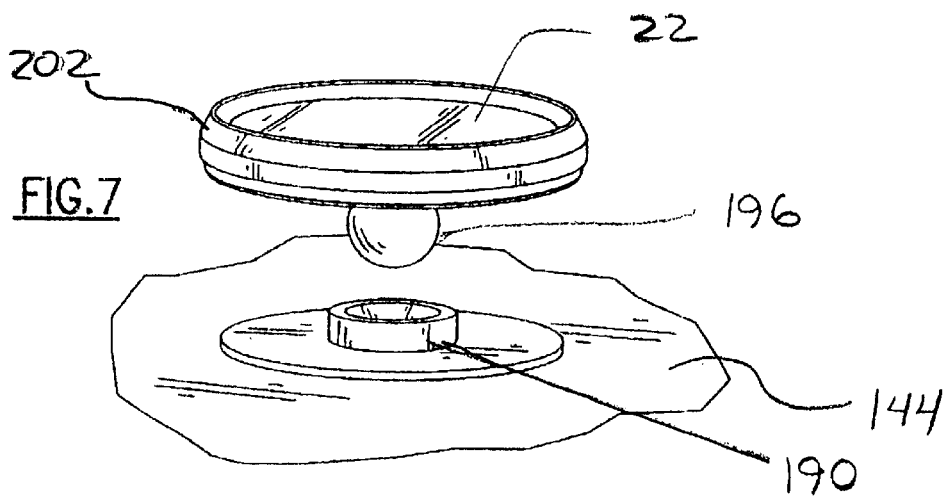
FIG. 7 is an unassembled view of the pressure measuring device of FIG. 6.
Figure 8:
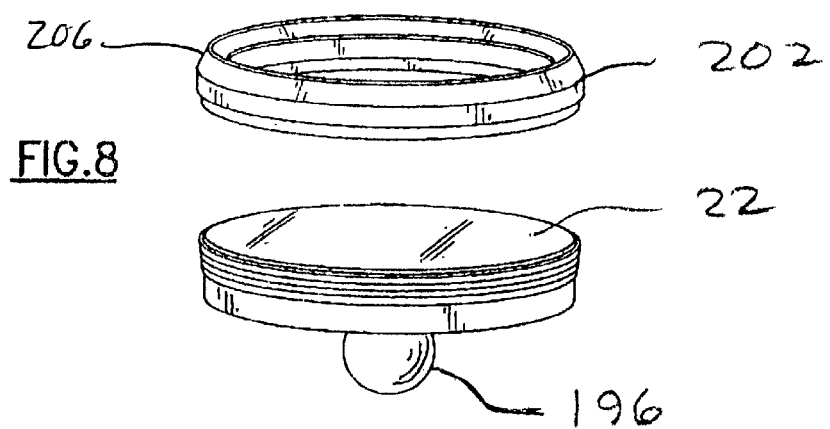
FIG. 8 is an exploded view of the housing of the housing of the pressure measuring device shown in FIGS. 6 and 7.

Referring to FIGS. 6–8, there is shown a blood pressure measuring device made in accordance with a fifth embodiment of the present invention. This device includes an RF blood pressure sleeve similar to that described in the previously incorporated '718 patent including a pair of sleeve portions 144 and 146 which are sealed together to form an integral structure and define an inflatable inner volume 148. The sleeve is sized to be wrapped around the arm or other limb of a patient (not shown) in a manner which is commonly known, and therefore requiring no further explanation. A socket 190 is disposed and fixed within a slot 192 provided in the exterior of the sleeve portion 144, the socket being sized to receive a mating portion of an instrument housing 194. The instrument housing 194 according to this embodiment is similar to those previously described including a narrowed bottom portion, but in which the bottom portion also includes a ball-shaped engagement or mating end 196. The ball-shaped engagement end 196 is fitted within the socket 190 of the sleeve in order to provide a direct connection therewith, the housing being free to pivot about the plane of the sleeve as shown by reference numeral 198. The engagement end 196 includes an opening 200 which permits fluid communication with the sleeve wherein fluid (air) can enter the housing to cause corresponding movement of the diaphragm and the components of the movement mechanism, in the manner previously described herein.

Preferably, the viewing window 22 of the housing includes an anti-reflective coating to reduce glare, with the user (physician or caregiver) or patient having the ability to either rotate the housing or to pivot same in order to effectively utilize the instrument and read the dial face.

Referring to FIGS. 7 and 8, the device further includes a rubberized ring-shaped guard or bumper 202 which is fitted about the periphery of the housing 194, the bumper having a ridge 206 which extends a predetermined distance above the viewing window 22. The bumper 202 performs at least two functions; first, and though the present device is ultra light weight, the bumper additionally absorbs shock or impact loads when the housing 194 is dropped. Second, the bumper 202 also prevents damage to the viewing window 22.

PARTS LIST FOR FIGS. 1–8

10 device
12 housing
14 interior cavity
16 circumferential inner wall
18 open top end
19 reflexed portion
20 bottom wall
21 outer edge-support plate
22 bubble (viewing window)
24 downwardly extending portion
26 bottom opening
28 support plate
28A support plate
30 top facing side
32 bottom facing side
34 central through opening
36 sleeve
36A sleeve
40 movement mechanism
42 diaphragm subassembly
44 diaphragm
45 circumferential ledge
46 O-ring
46B O-ring
47 outer edge
48 pan
49 wave-like surfaces
50 cavity
51 cavity
52 contact surface
53 top end
54 shaft
55 bottom end
56 tubular member
57 shoulder
58 top cap portion
59 end-ribbon spring
60 bottom end
61 end-ribbon spring
62 indicating member
63 dial face
63A dial face
64 outer tubular shell
65 O-ring
66 threads
67 slot
68 biasing spring
69 recess
70 ribbon spring member
72 one end
73 threads
75 threads
80 slot
81 housing
82 docking hub
84 diaphragm
86 horizontal support plate
88 bottom end
90 outer edge
92 O-ring
96 press-fitted sleeve
100 wave-like surfaces
104 biasing spring
114 slot
116 end
118 O-ring
140 housing
142 cuff
44 sleeve portion
146 sleeve portion
148 inner volume
152 upper portion
154 lower portion
156 intermediate portion
162 slot
165 support plate
166 detachable stethoscope attachment
167 dial face
170 arm
171 movement mechanism
174 extending attachment
176 port
178 hose
180 female connector
184 port 190 socket
192 slot
194 instrument housing
196 ball-shaped engagement end
198 direction
200 opening
202 peripheral bumper
206 ridge It will be readily apparent to those of ordinary skill in the field that other variations and modifications are possible within the spirit and scope of the invention as defined by the following appended claims. For example, the above assemblies can include multiple diaphragms or capsules, or other pressure sensitive elements, such as bourdon tubes or the like as required in certain pressure sensitive devices, with at least one or all of the diaphragms and/or housings being modified in the preceding manner to allow efficient positioning of the movement mechanism(s) therein.

We claim:

1. A shallow profile pressure measuring device, said device comprising:
   a compact housing having an interior cavity; and
   a sleeve sized to be fitted about a patient limb and having means for receiving said housing, said housing further including an indicator disposed in an upper portion and a narrowed lower portion sized to be fitted within said receiving means of said sleeve, said narrowed lower portion including a ball-shaped engagement member permitting said housing to be pivotally mounted to said sleeve and permit angled viewing of said indicator.

2. A device according to claim 1, including a pressure responsive element disposed within the interior cavity of said housing, said pressure responsive element including a narrowed portion fitted within the narrowed portion of said housing.

3. A device according to claim 2, including a movement mechanism interconnecting a movable surface of said pressure responsive element and said indicator.

4. A device according to claim 3, wherein said movement mechanism includes an axially displaceable shaft member and a ribbon spring member helically wound around an axial portion of said shaft member, said ribbon spring member being attached at one end to said shaft member and at an opposite end to a fixed portion of said housing, and in which one end of said axially displaceable shaft member is disposed in relation to the movable surface of said pressure responsive element and an opposing end is connected to said indicator such that movement of said movable surface causes circumferential movement of said indicator.

5. A device according to claim 4, wherein the receiving means of said sleeve includes a socket sized for receiving the narrow extending portion of said housing, said ball-shaped engagement end including a port in fluid communication with the sleeve for permitting fluid to enter therethrough based on pressure variations.

6. A pressure sensitive device according to claim 2, wherein said pressure responsive element is a diaphragm.

7. A pressure sensitive device according to claim 6, wherein said sleeve is a blood pressure cuff.

8. A pressure sensitive device according to claim 1, wherein said housing is both pivotally and rotatably mounted to said sleeve.

9. A pressure sensitive device according to claim 1, wherein said compact housing includes a peripheral bumper guard.

10. A pressure sensitive device according to claim 9, wherein said bumper guard is releasably attached to the upper portion of said housing.

11. A pressure sensitive device according to claim 9, wherein the upper portion of said compact housing includes a viewing window for viewing said indicator, said bumper guard being sized such that a portion of said guard extends above the upper portion of said housing and surrounds said viewing window.

12. A blood pressure measuring device comprising:
    a housing having an interior cavity; and
    an inflatable sleeve for wrapping around a patient limb, said housing including an indicator mounted within an upper portion of said housing, a pressure responsive element having at least one movable surface, and a movement mechanism disposed within said interior cavity interconnecting said at least one movable surface of said pressure responsive element and said indicator, said housing further including a narrow lower portion including a ball-shaped engagement end for engaging said sleeve such that the housing is pivotally mounted in relation to said sleeve.

13. A blood pressure measuring device according to claim 12, wherein said pressure responsive element is a diaphragm.

14. A blood pressure measuring device according to claim 13, wherein said sleeve is a blood pressure cuff.

15. A blood pressure measuring device according to claim 12, wherein said housing is both pivotally and rotatably mounted to said sleeve.

16. A blood pressure measuring device according to claim 12, wherein said housing includes a peripheral bumper guard.

17. A blood pressure measuring device according to claim 16, wherein said bumper guard is releasably attached to said housing.

18. A blood pressure measuring device according to claim 16, wherein said compact housing includes a viewing window, said bumper guard being sized such that a portion of said guard extends above and surrounds said viewing window.

19. Blood pressure measuring apparatus comprising:
    a compact narrow profile gage housing having a dial face and an engagement member; and
    an inflatable sleeve sized to be fitted about a patient limb, said sleeve including receiving means for receiving said engagement member of said gage housing wherein said gage housing can remain attached to said sleeve during the entirety of a blood pressure measurement procedure.

20. Apparatus according to claim 19, wherein said receiving means
    includes a socket provided on said inflatable sleeve, said socket being sized to retain the engagement member of said gage housing.

21. Apparatus according to claim 20, wherein said socket is disposed in a slot provided in a wall of said inflatable sleeve.

22. Apparatus according to claim 21, wherein said socket is RF welded within the slot of said sleeve.

23. Apparatus as recited in claim 19, wherein said gage housing is supported for rotation within said receiving means about a primary axis of said gage housing.

24. Apparatus according to claim 19, including a pressure responsive element disposed within an interior cavity of said gage housing, said pressure responsive element including a narrowed portion fitted within the engagement member of said housing.

25. Apparatus according to claim 24, including a movement mechanism interconnecting a movable surface of said pressure responsive element and a dial indicator provided on said dial face of said gage housing.

26. Apparatus according to claim 25, wherein said movement mechanism includes an axially displaceable shaft member and a ribbon spring member helically wound around an axial portion of said shaft member, said ribbon spring member being attached at one end to said shaft member and at an opposite end to a fixed portion of said housing, and in which one end of said axially displaceable shaft member is disposed in relation to the movable surface of said pressure responsive element and an opposing end is connected to said indicator such that movement of said movable surface causes circumferential movement of said indicator.

27. Apparatus according to claim 24, wherein said pressure responsive element is a diaphragm.

28. Apparatus according to claim 19, wherein said gage housing is both pivotally and rotatably mounted to said inflatable sleeve.

29. Apparatus according to claim 19, wherein said gage housing includes a peripheral bumper guard.

30. Apparatus according to claim 29, wherein said bumper guard is releasably attached to the exterior of said gage housing.

31. Apparatus according to claim 29, wherein said gage housing includes a viewing window, said bumper guard being sized such that a portion of said guard extends above and surrounds said viewing window.

* * * * *

UNITED STATES PATENT AND TRADEMARK OFFICE
CERTIFICATE OF CORRECTION

PATENT NO. : 6,422,086 B1  
DATED : July 23, 2002  
INVENTOR(S) : Raymond Dromms, Scott W. Osiecki, Richard Vivenzio, Raymond A. Lia, Scott S. Stearns, Dominick A. Danna and James M. Baxter It is certified that error appears in the above-identified patent and that said Letters Patent is hereby corrected as shown below:

<u>Title page,</u>
Item [75], Inventors, should read:

-- [75]  Inventors:  Raymond P. Dromms, Scott W. Osiecki, Robert L. Vivenzio, Raymond A. Lia, Scott S. Stearns, Dominick Danna, and James M. Baxter --

Signed and Sealed this

Nineteenth Day of November, 2002

Attest:

Attesting Officer

JAMES E. ROGAN  
*Director of the United States Patent and Trademark Office*